United States Patent [19]

Saito et al.

[11] Patent Number: 4,752,612

[45] Date of Patent: Jun. 21, 1988

[54] METHOD AND PERCUTANEOUSLY ADMINISTERING PHYSIOLOGICALLY ACTIVE AGENTS USING AN ALCOHOL ADJUVANT AND A SOLVENT

[75] Inventors: Kenichiro Saito; Jorge Heller; Wilfred Skinner, all of Menlo Park, Calif.

[73] Assignee: Nitto Electrical Industrial Co., Ltd., Japan

[21] Appl. No.: 824,393

[22] Filed: Jan. 23, 1986

Related U.S. Application Data

[63] Continuation-in-part of Ser. No. 510,133, Jul. 1, 1983, Pat. No. 4,590,190.

[51] Int. Cl.[4] ..................... A61U 31/19; A61U 31/40; A61U 31/195
[52] U.S. Cl. .................................. 514/420; 514/561; 514/570; 514/571

[58] Field of Search .............. 514/221, 556, 557, 420, 514/561, 570, 571, 567

[56] References Cited

FOREIGN PATENT DOCUMENTS 1518683  7/1978  United Kingdom .

Primary Examiner—Stanley J. Friedman
Attorney, Agent, or Firm—Sughrue, Mion, Zinn, Macpeak, and Seas

[57] ABSTRACT

A method of percutaneously administering a physiologically active agent which comprises applying to the skin of a mammal a physiologically active agent in a carrier system which comprises at least one adjuvant and at least one solvent. The adjuvant can be selected from higher monoalcohols or mixtures thereof. The solvent can be selected from thioglycerols, lactic acid and esters thereof, cyclic ureas, compounds represented by the general formula $R_1R_2NCONR_3R_4$, pyrrolidone-type compounds, amides, lactones or mixtures thereof.

4 Claims, No Drawings

METHOD AND PERCUTANEOUSLY ADMINISTERING PHYSIOLOGICALLY ACTIVE AGENTS USING AN ALCOHOL ADJUVANT AND A SOLVENT

CROSS-REFERENCE TO RELATED APPLICATION

This application is a continuation-in-part of U.S. application Ser. No. 510,133 filed July 1, 1983, now U.S. Pat. No. 4,590,190.

BACKGROUND OF THE INVENTION

1. Field of the Invention

The present invention relates to a method for accelerating the percutaneous absorption of a physiologically active agent (hereafter often merely an "active agent" for brevity).

2. Description of the Prior Art

Active agents are commonly administered to the skin or mucosal tissues to treat local problems and systemic administration of active agents is commonly accomplished by ingesting pills or by injections. However, recently attempts have been made to achieve systemic administration of active agents by topical applications to the skin or mucosal tissues. Such topical means of achieving systemic administration has the advantage that desired blood levels can be readily achieved and maintained so that duration of therapy can be readily controlled. Thus, side effects due to an overdose of the active agent can be prevented. Also, metabolism due to a first pass through the liver and gastric disturbances, which are characteristic of certain drugs such as indomethacin when administered orally, can also be eliminated.

However, normal skin is relatively impermeable to most therapeutic agents in that desired blood levels of the therapeutic agent cannot be achieved by means of percutaneous absorption. The percutaneous absorption of therapeutic agents can, however, be enhanced by means of adjuvants or penetration enhancers.

One of the best known of such penetrating adjuvants is dimethyl sulfoxide, the use of which is described in detail in U.S. Pat. No. 3,551,554 Herschler et al, which patent broadly suggests the use of dimethyl sulfoxide as a penetrating adjuvant for psychopharmacological drugs such as benzodiazepine derivatives.

British Pat. No. 1,504,302 Brooker et al deals with sedative methods and compositions and discloses the administration of sedatives by applying to the skin of a non-human animal a sedating amount of one or more sedative compounds in various penetrating adjuvants such as hydrocarbons such as aromatic hydrocarbons or paraffins, halogenated aliphatic hydrocarbons, ketones, esters, ethers, alcohols having from two to eight carbon atoms, amides, e.g., dimethyl acetamide, or sulfones. Brooker et al broadly indicates that one or more of the above liquids can be used in combination, but exemplify the halogenated aliphatic hydrocarbons only with carbon tetrachloride and exemplify the amides only with dimethylformamide.

Japanese Patent Application No. 52-148,614 (unexamined) Yonemushi discloses, without supporting data or explanation of substance, the use of sulfones by-produced in the refining of petroleum "as solvents to enhance the efficacy of drugs for skin disease" and "as drug penetration enhancers".

U.S. Pat. No. 4,202,888 Eckert et al discloses absorbable pharmaceutical compositions comprising at least one cardiac glycoside distributed in a vehicle comprising an absorption-enhancing amount of at least a partial glyceride of a fatty acid of medium chain length.

U.S. Pat. No. 3,472,931 Stoughton relates to percutaneous absorption using lower alkyl amides, and exemplifies binary systems which comprise dimethylacetamide and ethanol, dimethylacetamide and isopropyl alcohol and dimethylacetamide and isopropyl palmitate. Stoughton does not exemplify or disclose the combination of dimethylacetamide with higher molecular weight alcohols. At column 5 Stoughton suggests that emollients, including lanolin alcohols and fatty acid alcohols in general, give increased percutaneous absorption and increased retention, resulting in improved softening and moisturizing effects. The main components used in the percutaneous absorption system of Stoughton are amides, including N,N-dimethyl acetamide.

U.S. Pat. No. 3,969,516 Stoughton discloses compositions and methods for the treatment of acne comprising about 0.1 to about 10% by weight of an antibiotic of the lincomycin family. Stoughton lists a substantial number of additional ingredients which can be used in such formulations, including stearyl alcohol, and indicates that preferred ingredients include alcohols and other materials which enhance percutaneous absorption such as 2-pyrrolidone and N-lower alkyl substituted 2-pyrrolidones. In Example V formulations are prepared including, inter alia, N-methyl-2-pyrrolidone and stearyl alcohol. Stearyl alcohol is a $C_{18}$ alcohol which is solid at around 37° C.

U.S. Pat. No. 3,989,816 Rajadhyaksha discloses a method for carrying physiologically active agents through body membranes such as skin which comprise an effective, nontoxic amount of certain 1-substituted-azacycloheptan-2-ones. While not exemplified, the formula in Rajadhyaksha is broad enough to include, e.g. methyl caprolactam. Inert carriers may be used in the Rajadhyaksha composition. In Example 3 isopropyl myristate is used, in Example 5 stearyl alcohol is used (a $C_{18}$ alcohol having a melting point of 59° C.) and in Examples 8 and 11 cetyl alcohol is used (and $C_{17}$ alcohol having a melting point of 49° C.).

U.S. Pat. No. 4,017,641 DiGiulio deals with skin moisturizing compositions comprising 2-pyrrolidones which can be used with suitable oils and waxes including aliphatic straight chain fatty acids and alcohols of from about 10 to about 20 carbon atoms. This patent does not, however, deal with percutaneous administration of physiologically active agents.

European Patent Application No. 0043738 discloses binary percutaneous administration systems which comprise a monoglyceride, a diol or a diol ether in combination with a second component such as an alcohol, ester, amide or the like.

The present invention involves multicomponent carrier systems for the percutaneous administration of physiologically active agents which differ from the systems disclosed in the above prior art.

SUMMARY OF THE INVENTION

Per the present invention, it has been discovered that certain multicomponent carrier systems provide enhanced percutaneous administration of physiologically active agents.

The carrier sytems of the present invention comprise at least one adjuvant (Component A) and at least one solvent (Component B).

The adjuvant of the present invention is a higher aliphatic monoalcohol or a mixture of higher aliphatic monoalcohols. Any higher aliphatic monoalcohol used must have a melting point below 38° C.; accordingly, any higher aliphatic monoalcohol containing more than 14 carbon atoms must contain at least one unsaturated bond, at least one branched chain and/or at least one alicyclic group in the molecule thereof.

The solvents of the present invention are selected from thioglycerols, lactic acid or esters thereof, cyclic ureas, compounds represented by the general formula $R_1R_2NCONR_3R_4$, pyrrolidone-type compounds, amides, lactones or mixtures thereof.

Per the present invention, a physiologically active agent can be percutaneously administered by blending the same with a combination of Component A and Component B and applying the same to the skin.

The above-described compositions can be used as bases for medical preparations comprising active agents applicable to the outer skin.

One object of the present invention is to provide base compositions or percutaneous absorption enhancing combinations (often abbreviated as PAEC or PAECs hereafter) for medical preparations for external use which enhance the permeability of active agents through the skin and the percutaneous absorption of active agents.

A second object of the present invention is to provide pharmaceutical compositions comprising a PAEC for external use which provides good permeability of active agents through the skin and percutaneous absorption of active agents.

A third object of the present invention is to provide a method for enhancing the permeability of active agents through the skin and percutaneous absorption of active agents using a PAEC per the present invention.

In a preferred embodiment, the combination of the present invention which enhances percutaneous absorption comprises one or more higher aliphatic monoalcohols.

A fourth object of the present invention is to provide PAECs which ensure rapid transepidermal delivery of physiologically active agents in man or other animals.

A fifth object of the present invention is to provide such rapid transepidermal delivery which provides drug blood levels in the therapeutic range for the treatment of humans and other animals.

A sixth object of the present invention is to provide, through transepidermal delivery, at appropriately adjusted rates, relatively constant therapeutic blood levels so as to avoid the side effects and reduced therapeutic effects that may result from wide fluctuations in blood levels over time.

DESCRIPTION OF PREFERRED EMBODIMENTS

Examples of Component A include higher aliphatic monoalcohols having from 10 to 26 carbon atoms which may be branched, straight chain, saturated, unsaturated or cyclic and which may be primary, secondary, or tertiary.

As earlier indicated, any higher aliphatic monoalcohol must have a melting point below 38° C. and, accordingly, if the same contains more than 14 carbon atoms must contain at least one unsaturated bond, at least one branched chain and/or at least one alicyclic group in the molecule thereof, the terminology "at least one" reflecting the fact that, if desired, the higher aliphatic monoalcohol containing more than 14 carbon atoms can simultaneously meet two or three of these criteria.

Generally no more than about four or five unsaturated bonds, i.e., a carbon-carbon unsaturated bond, will be present in such a higher aliphatic monoalcohol, though this is not limitative. Further, while the at least one unsaturated bond is most preferably present in the main chain of the higher aliphatic monoalcohol, it can be present in a branched chain when a branched chain is present or in an alicyclic moiety when an alicyclic moiety is present.

The branched chain must contain at least one carbon atom, i.e., can be methyl. Typically, however, the branched chain will contain no more than about 13 carbon atoms in which, for a 26 carbon atom higher aliphatic monoalcohol, the branch and the main chain will have the same number of carbon atoms. The branched chain can contain the at least one unsaturated bond as above discussed and/or can contain the alicyclic moiety as now discussed.

Higher aliphatic monoalcohols containing more than 14 carbon atoms can also contain at least one alicyclic moiety which must be a non-aromatic ring. The alicyclic moiety must contain at least 3 carbon atoms and generally will contain no more than 12 carbon atoms. It is possible that more than one alicyclic moiety can be present, if desired, and, as earlier indicated, the alicyclic moiety, for example, a cyclohexyl group, can contain at least one unsaturated bond and may have at least one branched chain substituted thereon. The alicyclic group can be in the main or branched chain of the alcohol or substituted thereon.

In summary, the requirement that a higher aliphatic monoalcohol useful per the present invention which contains more than 14 carbon atoms must contain at least one unsaturated bond, at least one branched chain and/or at least one alicyclic group in the molecule thereof can be met by any of the above possibilities and it is to be understood that the at least one unsaturated bond and the at least one alicyclic group may be, but need not be, in the main chain of the higher aliphatic monoalcohol.

Examples of Component B include the following compounds:

(1) Thioglycerols:

Any mono-, di- and trithioglycerols can be used, an example of which includes α-monothioglycerol.

(2) Lactic acid and esters thereof:

As the alcohol moiety in the esters, monovalent aliphatic alcohols having 1 to 4 carbon atoms are preferred, specific examples of which include lactic acid, methyl lactate, ethyl lactate, butyl lactate, etc.

(3) Cyclic ureas:

5-Membered or 6-membered rings are preferred, specific examples of which include ethylene urea, N,N-dimethylethylene urea, and the corresponding propylene ureas, etc.

(4) Compounds represented by the general formula:

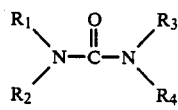

wherein $R_1$, $R_2$, $R_3$ and $R_4$ each represents a hydrogen atom, a lower alkyl group having 1 to 4 carbon atoms (methyl, ethyl, n-propyl, iso-propyl, n-butyl, etc.) or an acyl group having 1 or 2 carbon atoms:

Specific examples thereof include urea, N-methylurea, N-ethylurea, N-butylurea, 1,1-dimethylurea, 1,3-dimethylurea, 1,1,3,3-tetramethylurea, N-acetyl-N'-methylurea, etc.

(5) Compounds represented by the general formula:

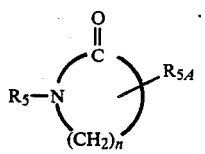

wherein $R_5$ represents a hydrogen atom or a lower alkyl group having 1 to 4 carbon atoms (methyl, ethyl, n-propyl, iso-propyl, etc.), $R_{5A}$ is hydrogen or a lower alkyl group having 1 to 3 carbon atoms and n represents an integer of 3 to 5:

Specific examples thereof include 2-pyrrolidone, N-methylpyrrolidone, N-methylpiperidone, caprolactam, N-methylcaprolactam, etc.

(6) Compounds represented by the general formula:

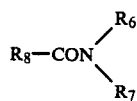

wherein $R_6$ represents a hydrogen atom or an alkyl group having 1 to 3 carbon atoms (methyl, ethyl, n-propyl, etc.) and $R_7$ and $R_8$ each represents an alkyl group having 1 to 3 carbon atoms, with the proviso that $R_6$, $R_7$ and $R_8$ have in total at least 3 carbon atoms:

Specific examples thereof include N,N-diethyl formamide, N,N-dimethylacetamide, N,N-diethylacetamide, N,N-dimethylpropionamide, N,N-diethylpropionamide, etc.

(7) Lactones having 4 to 6 carbon atoms:

Specific examples thereof include γ-butyrolactone, δ-valerolactone, etc.

In addition to the above, there are certain most preferred PAECs per the present invention, and these are discussed below.

We are unsure why the most preferred combination of PAECs of the present invention offers enhanced percutaneous absorption; however, the data we have generated indicate that there is a synergistic effect between the two groups of materials.

We consider the materials such as the higher aliphatic monoalcohols to basically serve an adjuvant function and materials such as the pyrrolidone-type compounds, amides, etc., to serve as solvents which enhance the solvating function of the adjuvant. We further believe that the solvents carry the active agent whereas the adjuvants open up the stratum corneum. We do not wish to be bound by these theories, and we merely use the terminology "solvent" and "adjuvant" to maintain a line of distinction between the two classes of materials which are mandatorily used in combination.

The preferred adjuvants as Component A of the present invention are aliphatic monoalcohols with from 10 to 24, most preferably 12 to 22, carbon atoms. The aliphatic monoalcohols may be branched chain, straight chain, saturated, unsaturated or cyclic.

The most preferred solvents as Component B include the pyrrolidone-type compounds and the amides.

The pyrrolidones are most preferably alkyl pyrrolidones of the formula:

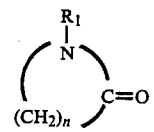

where $R_1$ is an alkyl group containing up to 4 carbon atoms and n is 3 to 5.

The amides are most preferably represented by the formula:

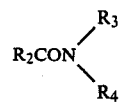

where $R_2$ can be hydrogen or an alkyl group with up to 3 carbon atoms and $R_3$ and $R_4$ can be an aliphatic group with up to 3 carbon atoms.

The base compositions of the present invention can be prepared by dissolving Component A in Component B. The amount of Component A to be used is generally from 0.1 to 80% by weight based on the total weight of Components A and B, preferably 0.5 to 50% by weight. Of course, pharmaceutically acceptable additives such as water, etc., can also be added to the base compositions.

The pharmaceutical compositions for topical application per the present invention can be prepared by blending active agents with the above-described base compositions. There is no particular limit on the active agents used so long as the active agents are systemically active and percutaneously applicable.

Specific examples of active agents include benzodiazepines (e.g., Diazepam, Nitrazepam, Flunitrazepam, Lorazepam, Fludiazepam, Clonazepam), diuretic agents [e.g., thiazides (e.g., Bendroflumethiazide, Polythiazide, Methyclothiazide, Trichloromethiazide, Cyclopenthiazide, Bentylhydrochlorothiazide, Hydrochlorothiazide, Bumetanide)], antihypertensive agents (e.g., Clonidine), antihistamic agents [e.g., aminoethers (e.g., diphenhydramine, Carbinoxamine, Diphenylpyraline), ethylenediamines (e.g., Fenbenzamine), monoamines (e.g., Chlorophenylamines)], non-steroid antiinflammatory agents (e.g., Indomethacin, Ibuprofen, Ibufenac, Alclofenac, Diclofenac, Mefenamic acid, Flurbiprofen, Flufenamic acid, Ketoprofen), anti-tumor agents (e.g., 5-fluorouracil, 1-(2-tetrahydrofuryl)-5-fluorouracil, Cytarabine, Floxuridine). Steroid antiinflammatory agents (e.g., Cortisone, Hydrocortisone, Prednisolone, Predonisone, Triamcinolone, Dexamethasone, Betamethasone), antiepileptic agents (e.g., Ethosuximide), antiarrythmic agents (e.g., Ajmalin, Purajmalin. Pindolol, Propranolol, Quinidine), psychotropic agents [e.g., Clofluperol, Trifluperidol, Haloperidol, Moperone), scopolamines (e.g., methyl scopolamine, butyl scopolamine), metoclopramide, chlorpromazine, atropines (e.g., methyl atropine bromide, methylanisotropine bromide), vascular dilating agents (e.g., isosorbide dinitrate, nitroglycerine, pentaerythritol tetranitrate, propanyl nitrate, dipyridamole), antibiotics, e.g., tetracyclines (e.g., Tetracycline, Oxytetracycline, metacycline, doxycycline, Minocycline), chloramphenicols, erythromycines], etc. The method of the present invention can also be utilized to percutaneously administer peptides such as LH-RH, insulin and the like. Of course, pharmaceutically acceptable salts such as the hydrochloride, sodium, potassium, hydrobromide, etc., salts can be used.

Since the present invention is of particular application with respect to the benzodiazepine materials, these are discussed in more detail below. Particularly preferred benzodiazepine materials are those which illustrate the benzodiazepine skeleton as schematically illustrated as follows:

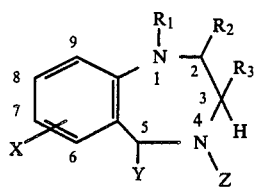

wherein X is Cl, Br, or $NO_2$, and Y is

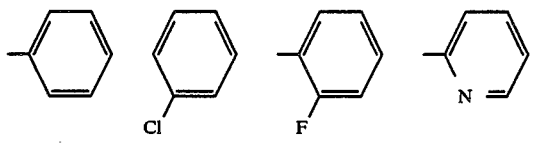

with varying degrees of unsaturation and substitution at positions 1, 2, 3, 4, and 5 as follows:

(a) 1, 2 and 4, 5 are unsaturated: $R_1$ and $R_3$ are H; $R_2$ is

(R is H or $CH_3$) and N—Z is N→O.

(b) 1, 2 are saturated and 4, 5 are unsaturated: $R_3$ is H or OH; —$R_2$ is —H or =O or =N*; $R_1$ is

(R is H, $CH_3$ or

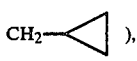), or $CH_2$—$CH_2$—$N(C_2H_5)_2$ or $R_1$ is C(R)=N* (R is H or $CH_3$) and is joined to $R_2$ via "*" (a single bond) as follows.

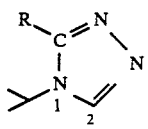

(c) 1, 2 and 4, 5 are saturated: $R_1$ is H; —$R_2$ is =O; $R_3$ is H and positions 4 and 5 constitute a second ring system as follows:

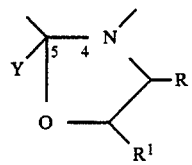

where R and $R^1$ are H and $CH_3$.

Specific examples of benzodiazepines which can be percutaneously administered using the active ingredient/penetration adjuvant combinations of the present invention include:

(a) Chlordiazepoxide; 7-Chloro-2-methylamino-5-phenyl-3H-1,4-benzodiazepine-4-oxide (b) Diazepam; 7-Chloro-1,3-dihydro-1-methyl-5-phenyl-2H-1,4-benzodiazepine-2-one (c) Oxazepam; 7-Chloro-1,3-dihydro-3-hydroxy-5-phenyl-2H-1,4-benzodiazepine-2-one (d) Temazepam; 7-Chloro-1,3-dihydro-3-hydroxy-1-methyl-5-2H-1,4-benzodiazepine-2-one (e) Lorazepam; 7-Chloro-5-(o-chlorophenyl)-1,3-dihydro-3-hydroxy-2H-1,4-benzodiazepine-2-one (f) Prazepam; 7-Chloro-1-cyclopropylmethyl-1,3-dihydro-5-phenyl-2H-1,4-benzodiazepine-2-one (g) Fludiazepam; 7-Chloro-1,3-dihydro-5-(2-fluorophenyl)-1-methyl-2H-1,4-benzodiazepine-2-one (h) Flurazepam; 7-Chloro-1-(2-(dimethylamino)ethyl)-5-(o-fluorophenyl)-1,3-dihydro-2H-1,4-benzodiazepine-2-one (i) Medazepam; 7-Chloro-2,3-dihydro-1-methyl-5-phenyl-1H-5,4-benzodiazepine (j) Bromazepam; 7-Bromo-5-(2-pyridyl)-3H-1,4-benzodiazepine-2(1H)-one (k) Nitrazepam; 1,3-Dihydro-7-nitro-5-phenyl-2H-1,4-benzodiazepine-2-one (l) Nimetazepam; 1-Methyl-7-nitro-5-phenyl-1,3-dihydro-2H-1,4-benzodiazepine-2-one (m) Clonazepam; 5-(o-Chlorophenyl)-7-nitro-1H-1,4-benzodiazepine-2(3H)-one (n) Flunitrazepam; 5-(o-Fluorophenyl)-1,3-dihydro-1-methyl-7-nitro-2H-1,4-benzodiazepine-2-one (o) Estazolam; 8-Chloro-1,6-phenyl-4H-s-triazolo(4,3-)(1,4)-benzodiazepine (p) Triazolam; 8-Chloro-6-(o-chlorophenyl)-1-methyl-4H-S-triazolo(4,3-)(1,4)-benzodiazepine (q) Alprazolam; 8-Chloro-1-methyl-6-phenyl-4H-s-triazolo(4,3-)(1,4)-benzodiazepine (r) Oxazolam; 10-Chloro-2,3,5,6,7,11b-hexahydro-2-methyl-11b-phenylbenzo(6,7)-1,4-diazepino(5,4-b-oxazol-6-one (s) Cloxazolam; 10-Chloro-11b-(o-chlorophenyl)-2,3,5,6,7,11b-hexahydrobenzo(6,7)-1,4-diazepino-(5,4-b)oxazol-6-one (t) Haloxazolam; 10-Bromo-11b-(o-fluorophenyl)-2,3,7,11b-tetrahydro-oxazolo(3,2,-d)(1,4)benzodiazepine-6(5H)-one Especially preferred are benzodiazepines (b), (e), (i), (k), (l), (n) and (o).

The amount of active agent(s) blended is sufficient if it is effective for achieving the desired pharmaceutical effect, which varies depending upon the kind of active agents, body weight of the patient, symptoms, etc. The amount may thus be suitably chosen depending upon these conditions. In general, it is preferred that active agents be employed in an amount of 0.01 to 50% by weight, more preferably 0.05 to 10% by weight, based on the total amount of the PAEC comprising Component A and Component B.

The dose of the active agents administered can be controlled by increasing or decreasing the area of skin to which the pharmaceutical compositions are applied. Accordingly, the amount of the active agent is not necessarily limited to the above-described ones.

As will be apparent to one skilled in the art, with increasing concentrations of active agent increasing amounts of active agent will be absorbed by the subject. The following discussion is given in terms of blood levels of drug (ng/ml of plasma), this being dependent upon the total area of dermal application, as there is a substantially linear increase in amount of active agent absorbed with area.

For a constant area of application and a constant absolute amount of adjuvant, the blood level of active agent at any given time is a function of the concentration of active agent in the composition. That is, increased concentrations of active agent in the formulation result in more rapid active agent penetration and higher blood levels.

A further factor which must be considered is that the amount of active agent absorbed will depend on the site of application, for example, scalp, ventral forearm, behind the ear, chest, etc. Typically an area rich in blood vessels is selected.

For most applications, the concentration of active agent in the PAEC will generally be on the order of 0.01 to 50%, the amount of PAEC applied will be about 0.1 mg to 100 mg per $cm^2$ and the total area of application will be on the order of about 0.5 $cm^2$ to about 100 $cm^2$, which will provide therapeutic blood levels of the desired active agent.

These ranges are not, however, to be considered as limitative.

In general, the rate of transepidermal active agent absorption will approach the rate of oral absorption depending upon the factors previously discussed (nature and amount of PAEC, concentration of active agent in the formulation, and surface area of skin application). Thus, peak blood levels of the active agent may be reached more slowly or at about the same rate and will reach about the same level as those obtained by oral administration. Alternatively, the blood level of active agent attained by single dose oral administration may be maintained for an extended period by subsequent percutaneous administration of the active agent. In the latter case, the initial oral dose may be smaller than the normal therapeutic oral dose so that side effects associated with higher-than-minimal therapeutic blood levels attained by a reduced oral dose may be maintained by the subsequent transepidermal administration at a proper rate.

Therapeutic oral doses of diazepam in man produce blood levels of approximately 100 ng/ml plasma [S. A. Kaplan, M. L. Jack, K. Alexander, and R. E. Weinfield, J. Pharm. Sci., 62, 1789–1796 (1973)]. Such a blood level is easily attainable by percutaneous administration by way of the present invention and produces pharmacological (behavioral) signs of therapeutic effectiveness in appropriate animal models for man, e.g., the rhesus monkey.

The method of the present invention finds application with mammals in general, most particularly man and domestic animals such as cows, sheep, horses, dogs, cats and the like.

The pharmaceutical composition of the present invention is administered to the outer skin as a simple mixture or as a medical preparation by adding known pharmaceutically acceptable third components in the form of solutions, ointments (paste-including creams and gels) lotions, adhesive tapes, a plaster, etc.

For example, solutions may simply comprise the active agent dissolved in the PAEC with optional components, e.g., glycerin, and the solutions may be incorporated into absorbents, e.g., a gauze, porous membrane, etc.

Ointments, gels or creams may contain conventional ingredients (e.g., polyethylene glycol and hydroxy propylcellulose, etc.) to form the same, and the same may be spread onto backing materials, e.g., a plastic film. Similarly, plasters or adhesives tapes may contain the active agent and PAEC in an adhesive base, e.g., acrylic copolymers or other synthetic gums.

The above listed components should be substantially inert in the system and not increase or decrease the effect of the PAEC.

The PAEC may be added to such a composition in varying amounts as desired, generally from 10 to 99% by weight.

In developing the present invention, we have used both diffusion cells and an animal model. The diffusion cell methods provided a qualitative assessment of the active agent/PAEC effect on percutaneous absorption. The animal model rhesus monkey test also provides an acceptable pharmacokinetic model for man as indicated by J. Soc. Cosmet. Chem., 30, 297–307. September/October 1979 and Toxicol. Appl. Pharmacol., 32, 394–398, 1975.

EXPERIMENTAL

In Vitro Skin Penetration Studies with Diffusion Cell Technique

Rat full thickness skins were used in the diffusion cell method following the method of Michaels, AIChE Journal, 21 [5], 985–996, 1975. The rat skin was mounted in the diffusion cell in a vertical position between the upstream and the downstream compartments; the exposed area of the skin approximated 4.15 $cm^2$.

The skin was excised from the shaved abdominal site of male albino rats weighing 250~300 g, and washed with normal saline solution after the subcutaneous fat was carefully removed with scissors.

The active agent/PAEC solution of known concentration was added to the upper compartment of the cell, which was exposed to the epithelial side of the skin and a normal saline solution was placed in the lower compartment.

The penetration rate was studied in a thermostated bath at 30° C. At appropriate intervals samples were withdrawn from the lower compartment and subsequently analyzed for active agent concentration by standard analytical methods.

As an alternative, the finite dose technique of Franz, Curr. Probl. Dermatol., Vol. 7, p. 58–68 (Karger, Basel, 1978) can also be followed where the rat skin is mounted horizontally in a diffusion cell apparatus and the exposed area of the skin approximates 0.7 cm².

The active agent/PAEC solution of known concentration was added to the upstream compartment to which the epithelial side of the skin was exposed, and a normal saline solution was added to the downstream compartment.

In Vivo Rhesus Monkey Test

If desired, an in vivo rhesus monkey test as described below may also be used to determine the effect of the PAEC combinations of the present invention.

Male rhesus monkeys weighing 10-14 Kg each can be used as the subject. An appropriate area of the monkey's chest is shaved 24 hours before drug application.

Drug formulations comprising the PAEC are applied to a certain area of the chest. The monkey is restrained in a chair to prevent it from touching its chest.

Blood samples are taken at appropriate intervals after the application. The heparinized blood is centrifuged, and the plasma removed and stored at −20° C. until analyzed.

Diazepam in plasma can be analyzed following the GLC method of Aingales, J. Chromatog., 75, 55-78, 1973.

Hereafter the present invention will be illustrated with reference to the examples and experiments in more detail, but it is not to be deemed to be limited thereto.

Liquid compositions are prepared by firstly mixing Component A with Component B and then blending the active agent in the mixture. In the case that Component B is a solid at ambient temperature or will not homogenously mix with Component A, 20 wt.% of ethylene glycol monobutyl ether based on the weight of Components A and B can be used as an agent for assisting dissolution.

Further, in the following examples, the abbreviations below are used:
EtOH—ethanol
MP—1-methyl-2-pyrrolidone
$C_{12}OH$—dodecanol
DMAc—dimethyl acetamide Unless otherwise indicated, in all of the following examples the active agent is diazepam or metoclopramide hydrochloride. The flux of the active agent is given in terms of $\mu g/cm^2/8$ hours. Twenty-five volume percent Component A with respect to Component A plus Component B volume was used in the composition along with 2.5 weight percent of the active agent. For purposes of comparison, in certain instances the results for solvents alone and adjuvants alone are given.

EXAMPLE 1

The results of this example (in Table 1) show the use of a pyrrolidone as Component B in combination with various aliphatic alcohols as Component A which are saturated, unsaturated, straight, branched and/or cyclic. Also, as a comparison, Table 1 contains the use of MP or n-dodecanol alone and the use of MP in combination with aliphatic alcohols, octanol and cyclohexyl ethanol, as a component outside of this invention.

TABLE 1

| Component B | Component A | Diazepam Flux ($\mu g/cm^2/8$ hrs) |
|---|---|---|
| N—methyl-2-pyrrolidone | — | 94 |
| — | 1-dodecanol | 24 |
| N—methyl-2-pyrrolidone | 1-octanol | 191 |
| N—methyl-2-pyrrolidone | 1-cyclohexyl ethanol | 176 |
| N—methyl-2-pyrrolidone | 4-cyclohexyl 1-butanol | 238 |
| N—methyl-2-pyrrolidone | 1-dodecanol | 403 |
| N—methyl-2-pyrrolidone | oleyl alcohol | 871 |
| N—methyl-2-pyrrolidone | 2-octyl-1-dodecanol | 460 |

EXAMPLE 2

An active agent other than diazepam with a combination of a pyrrolidone and an aliphatic alcohol was studied.

A propranolol system was formulated as follows: 10 mg of propranolol was dissolved in 1 ml of 25 volume % dodecanol in N-methyl-2-pyrrolidone (based on total volume) and in 1 ml of ethyl alcohol as a comparison study.

The flux rates for 8 hours are shown in Table 2.

TABLE 2

| Compositions | Flux ($\mu g/cm^2/8$ hrs) |
|---|---|
| Propranolol in $C_{12}OH$/MP | 159 |
| Propranolol in EtOH | 30 |

EXAMPLE 3

This example shows the use of an amide as Component B in combination with various aliphatic alcohols as Component A in a manner similar to Example 1.

The flux rates for 8 hours are shown in Table 3.

TABLE 3

| Component B | Component A | Diazepam Flux ($\mu g/cm^2/8$ hrs) |
|---|---|---|
| N,N—dimethyl acetamide | — | 139 |
| — | 1-dodecanol | 24 |
| N,N—dimethyl acetamide | 1-decanol | 302 |
| N,N—dimethyl acetamide | 2-octyl-1-dodecanol | 516 |
| N,N—dimethyl acetamide | phytol | 499 |
| N,N—dimethyl acetamide | 2-decyl-1-tetradecanol | 379 |

EXAMPLE 4

This example shows the use of 1-dodecanol as the adjuvant in combination with various pyrrolidones as the solvent and also with 1-benzyl-2-pyrrolidone as a comparison study. Metoclopramide HCl was used as the active agent. The flux rates for 8 hours as shown in Table 4:

TABLE 4

| Adjuvant | Solvent | Metoclopramide HCl Flux ($\mu g/cm^2/8$ hrs) |
|---|---|---|
| 1-dodecanol | 2-pyrrolidone | 1668 |
| 1-dodecanol | 2-methyl-2-pyrrolidone | 3160 |
| 1-dodecanol | 1-ethyl-2-pyrrolidone | 2884 |
| 1-dodecanol | 1,5-dimethyl-2-pyrrolidone | 2060 |

TABLE 4-continued

| Adjuvant | Solvent | Metoclopramide HCl Flux ($\mu g/cm^2/8$ hrs) |
|---|---|---|
| 1-dodecanol | 1-benzyl-2-pyrrolidone | less than 10 |

EXAMPLE 5

This example shows a comparison of the flux rate for 8 hours between metoclopramide (free base) and its HCl salt with a combination of 1-dodecanol and 1-methyl-2-pyrrolidone. Results are given in Table 5.

TABLE 5

| Composition | Flux ($\mu g/cm^2/8$ hrs) |
|---|---|
| Metoclopramide (free base) in $C_{12}OH/MP$ | 2694 |
| Metoclopramide HCl in $C_{12}OH/MP$ | 3280 |

EXAMPLE 6

Table 6 shows the relative flux of metoclopramide HCl with 25% of various alcohols in MP compared to the flux with 25% $C_{12}OH$ in MP. Also, as a comparison, the relative flux with 25% tetraethylene glycol in MP compared to 25% $C_{12}OH$ in MP is shown.

TABLE 6

|  | Relative Flux |
|---|---|
| tetraethylene glycol in MP | less than 0.1 |
| 1-dodecanol in MP | as 1 |
| phytol in MP | 0.7 |
| 2-octyl-1-dodecanol in MP | 0.5 |

EXAMPLE 7

Table 7 shows the relative metoclopramide HCl flux with lower concentrations of $C_{12}OH$ in MP compared to the flux with 25% $C_{12}OH$ in MP.

TABLE 7

|  | Relative Flux |
|---|---|
| 25% $C_{12}OH$ in MP | as 1 |
| 10% $C_{12}OH$ in MP | 1.0 |
| 5% $C_{12}OH$ in MP | 0.7 |
| 1% $C_{12}OH$ in MP | 0.6 |
| 0% $C_{12}OH$ in MP | 0.1 |

In addition to the earlier exemplified materials, the following examples further illustrate the application of the PAEC of the present invention with respect to Beta blockers (e.g., propranolol) and calcium antagonists (e.g., verapamil, Nifedipine), etc.

In the following Example 8, in vitro transdermal penetration was again analyzed using rat full thickness skins following the method of Michaels, AIChE Journal, 21, [53], pp. 985-996 (1975), according to the procedure earlier described. The sample volume was 1 ml unless otherwise indicated and flux of the active agent is given in $\mu g/cm^2/8$ hours. All percents are volume percents based on the total volume of the system unless otherwise indicated.

EXAMPLE 8

This Example illustrates the use of propranolol, commercially available as Pindolol, and shows the flux of Pindolol for 8 hours with combinations of various alcohols and N-methyl pyrrolidone (MP).

The Pindolol vehicle combinations were:
(a) 25 mg Pindolol + 1 ml of 25% 3-octanol and 75% MP.
(b) 25 mg Pindolol + 1 ml of 25% 1-dodecanol and 75% MP.
(c) 25 mg Pindolol + 1 ml of 25% oleyl alcohol and 75% MP.

The results were:
(a) 1145 ($\mu g/cm^2/8$ hours)
(b) 1559
(c) 1199

The following Examples 9 to 11 show the flux of nonsteroidal anti-inflammatory drugs (NSAIDs).

EXAMPLE 9

The physiologically active agent was Indomethacin, a commercially available NSAID, which is 1-(p-chlorobenzoyl)-5-methoxy-2-methylindole-3-acetic acid.

The following combinations were used:
(a) 25 mg Indomethacin + 1 ml of 25% linalool and 75% MP.
(b) 25 mg Indomethancin + 1 ml of 25% 1-dodecanol and 75% MP.
(c) 25 mg Indomethacin + 1 ml of 25% oleyl alcohol and 75% MP.

The results were:
(a) 98 ($\mu g/cm^2/8$ hours)
(b) 236
(c) 236

EXAMPLE 10

The physiologically active agent was Diclofenac, a commercially available NSAID which is sodium 2-(2,6-dichloroanilino)phenylacetate.

The following combinations were used:
(a) 25 mg Diclofenac + 1 ml of 25% 1-dodecanol and 75% MP.
(b) (Comparison) 25 mg Diclofenac + 1 ml of dimethyl sulfoxide (DMSO).

The results were:
(a) 368 ($\mu/cm^2/8$ hours)
(b) 107

EXAMPLE 11

The physiologically active agent was the NSAID Ibuprofen, commercially available from Upjohn, which is p-isobutylhydratropic acid <2',4'-isobutylphenyl propionic acid.

The following combinations were used:
(a) 25 mg Ibuprofen + 1 ml of 25% 1-dodecanol and 75% N-methyl pyrrolidone.
(b) 25 mg Ibuprofen + 1 ml of 25% 1-dodecanol in 75% N-methyl piperidone.
(c) 25 mg Ibuprofen + 1 ml of 25% 1-dodecanol in 75% N-methyl caprolactum.

The results were:
(a) 307 ($\mu g/cm^2/8$ hours)
(b) 266
(c) 148

The following Examples 12 and 13 illustrate th flux of calcium antagonists.

EXAMPLE 12

The physiologically active agent was Verapamil which has the formula:

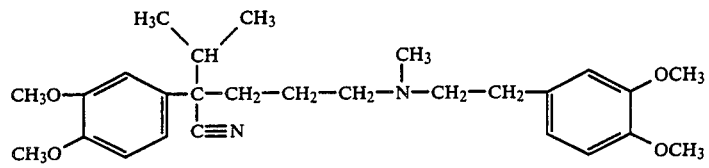

The following combinations were used:
(a) 25 mg Verapamil+1 ml of 25% 1-dodecanol and 75% MP.
(b) (Control) 25 mg Verapamil+1 ml of N-methyl pyrrolidone (MP).
(c) (Comparison) 25 mg Verapamil+1 ml of dimethyl sulfoxide (DMSO).
The results were:
(a) 1702 ($\mu$g/cm$^2$/8 hours)
(b) less than 10
(c) 38

EXAMPLE 13

The physiologically active agent was Nifedipine which is 1,4-dihydro-2,6-dimethyl-4-(2-nitrophenyl)-3,5-pyridine dicarboxylic acid dimethyl ester.
The following combinations were used:
(a) 25 mg Nifedipine+1 ml of 25% 1-dodecanol and 75% MP.
(b) 25 mg Nifedipine+1 ml of 25% oleyl alcohol and 75% MP.
(c) 25 mg Nifedipine+1 ml of 25% 2-octyl-1-dodecanol and 75% MP.
(d) (Control) 25 mg Nifedipine+1 ml of MP.
The results were:
(a) 480 ($\mu$g/cm$^2$/8 hours)
(b) 394
(c) 246
(d) 30

EXAMPLE 14

The physiologically active agent was Theophylline, an anti-asthmatic drug.
The combinations were:
(a) 400 mg Theophylline+1 ml of 25% 1-dodecanol and 75% N-methyl pyrrolidone (MP).
(b) 400 mg Theophylline+1 ml of 25% 1-dodecanol and 75% N-methyl caprolactum.
(c) (Comparison) 400 mg Theophylline+1 ml of dimethyl sulfoxide (DMSO).
(d) (Comparison) 400 mg Theophylline+1 ml of ethyl alcohol.
The results were:
(a) 6816 ($\mu$g/cm$^2$/8 hours)
(b) 7906
(c) 1244
(d) 84

In the following Examples 15 and 16, the in vivo monkey regimen earlier described was used to determine the effect of the PAEC combinations of the present invention, the regimen being modified as follows:

Male rhesus monkeys weighting 8 to 13 Kg wee used as the subject and an appropriate area of the monkey's upper back was shaved 24 hours before drug application;

the drug formulations were applied to 49 cm$^2$ of the upper back of the monkey; and plasma samples taken at appropriate intervals were analyzed by conventional HPLC.

EXAMPLE 15

This Examples shows the in vivo plasma level of propranolol, a Beta-blocker, using the described topical formulation.

1 ml of 25% 1-dodecanol and 75% MP containing 200 mg of propanolol was impregnated into a polyester non-woven cloth (49 cm$^2$; 230 mg) and applied to the upper back area of the monkey.

The application site was occluded with Saran ® film.

| Drug | Plasma Level (ng/ml Plasma) | | | |
|---|---|---|---|---|
| | 1 hr | 3 hr | 5 hr | 7 hr |
| Propranolol | 0 | 55 | 85 | 80 |

EXAMPLE 16

The procedure of Example 15 was followed except for using Indomethacin, a NSAID, in place of propranolol.

| Drug | Plasma Level (ng/ml Plasma) | | | |
|---|---|---|---|---|
| | 1 hr | 3 hr | 5 hr | 7 hr |
| Indomethacin | 0 | 270 | 495 | 336 |

While there have been described what are at present considered to be the preferred embodiments of this invention, it will be obvious to those skilled in the art that various changes and modifications can be made therein without departing from the invention, and it is, therefore, intended to cover all such changes and modifications as fall within the true spirit and scope of the invention.

What is claimed is:

1. A method for percutaneously administering a non-steroid anti-inflammatory agent to a mammal which comprises applying the non-steroid anti-inflammatory agent to the skin of the mammal in a mixture comprising at least one of the following Components A and at least one of the following Components B:

Component A: an aliphatic monoalcohol having from 10 to 26 carbon atoms and mixture thereof;
Component B: a compound represented by the formula:

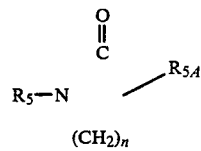

wherein R$_5$ represents a hydrogen atom or a lower alkyl group having 1 to 4 carbon atoms and n represents an integer of 3 to 5, R$_{5A}$ is hydrogen or a lower alkyl group having 1 to 3 carbon atoms, wherein Components A and B are present in an amount effective to enhance percutaneous absorption within the range of therapeutically effective rates, wherein the amount of Component A is from 0.1 to 80% by weight based on the total weight of Components A and B and wherein the amount of the non-steroid anti-inflammatory agent is from 0.01 to 50% by weight, based on the total amount of Component A and Component B.

2. The method of claim 1 wherein Component A is selected from an aliphatic monoalcohol having from 12 to 22 carbon atoms and mixtures thereof, and wherein Component B is selected from the group consisting of pyrrolidone-type compounds represented by the formula:

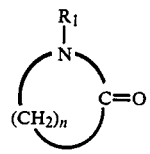

where n is 1 to 3 and $R_1$ is an alkyl group containing from 1 to 4 carbon atoms.

3. The method of claim 1 wherein Component A is 1-dodecanol and Component B is selected from the group consisting of: 2-pyrrolidone, 2-methyl-2-pyrrolidone, 1-ethyl-2-pyrrolidone and 1,5-dimethyl-2-pyrrolidone.

4. The method of claim 1, where Component A is 1-dodecanol and Component B is 2-methyl-2-pyrrolidone.

* * * * *